(12) United States Patent
Zeigler

(10) Patent No.: US 11,781,111 B2
(45) Date of Patent: Oct. 10, 2023

(54) ACTIVATION OF IMMUNE CELLS

(71) Applicant: Breakthrough Tech LLC, Aliso Viejo, CA (US)

(72) Inventor: Francis Christopher Zeigler, Carlsbad, CA (US)

(73) Assignee: Breakthrough Tech LLC, Aliso Viejo, CA (US)

(*) Notice: Subject to any disclaimer, the term of this patent is extended or adjusted under 35 U.S.C. 154(b) by 0 days.

(21) Appl. No.: 16/716,339

(22) Filed: Dec. 16, 2019

(65) Prior Publication Data

US 2020/0115679 A1    Apr. 16, 2020

Related U.S. Application Data

(62) Division of application No. 16/160,006, filed on Oct. 15, 2018, now Pat. No. 10,508,262.

(60) Provisional application No. 62/691,775, filed on Jun. 29, 2018.

(51) Int. Cl.
*C12N 5/078*     (2010.01)
*A61M 1/00*      (2006.01)
*A61K 35/17*     (2015.01)

(52) U.S. Cl.
CPC ............ *C12N 5/0634* (2013.01); *A61K 35/17* (2013.01); *A61M 1/84* (2021.05); *A61M 2202/10* (2013.01); *A61M 2205/7545* (2013.01); *C12N 2501/90* (2013.01); *C12N 2501/905* (2013.01)

(58) Field of Classification Search
None
See application file for complete search history.

(56) References Cited

U.S. PATENT DOCUMENTS

| | | | |
|---|---|---|---|
| 5,646,004 A | 7/1997 | Van Vlasselaer | |
| 6,838,086 B1 | 1/2005 | Simon et al. | |
| 9,188,588 B2 | 11/2015 | Baniyash et al. | |
| 10,508,262 B1 | 12/2019 | Zeigler | |
| 2016/0243165 A1 | 8/2016 | Stasko et al. | |
| 2018/0125894 A1 | 5/2018 | Sabaawy | |

FOREIGN PATENT DOCUMENTS

| | | |
|---|---|---|
| CN | 106727810 A | 5/2017 |
| WO | WO-2005079581 A1 | 9/2005 |

OTHER PUBLICATIONS

GE Healthcare Life Sciences; "Isolation of mononuclear cells: Methodology and applications" 2014 (Year: 2014).*
Fraser, J. R. et al., "Viscous interactions of hylaronic acid with some proteins and neutral saccharides," Ann. Rheum. Dis., 31(6):513-520 (1972).
Huang, D. et al., "A novel polysaccharide from the seeds of *Plantago asiatica* L. induces dendritic cells maturation through toll-like receptor 4," Int Immunopharmacol., 18(2):236-243 (2014). doi: 10.1016/j.intimp.2013.11.024. Epub Dec. 5, 2013.
Kovtun, A. et al., "The crucial role of neutrophil granulocytes in bone fracture healing," Eur Cell Mater., 32:152-62 (2016). doi: 10.22203/ecm.v032a10.
Lai, Ching-Yi et al., "Type II arabinogalactan from Anoectochilus formosanus induced dendritic cell maturation through TLR2 and TLR4," Phytomedicine, 22(14):1207-1214. doi: 10.1016/j.phymed. 2015.10.010. Epub Nov. 10, 2015.
Palucka, K. & Banchereau, J., "Dendritic-cell-based therapeutic cancer vaccines," Immunity, 39(1):38-48 (2013). doi: 10.1016/j.immuni.2013.07.004.
Shirali, A. C. & Goldstein, D. R., "Activation of the innate immune system by the endogenous ligand hyaluronan," Current Opinion in Organ Transplantation, 13(1):20-25 (2008).
Dearman, R. J. et al., "Toll-like receptor ligand activation of murine bone marrow-derived dendritic cells," Immunology, Apr. 2009; 126(4): 475-84. Epub Sep. 4, 2008.
Górska, S. et al., "Distinct immunomodulation of bone marrow-derived dendritic cell responses to Lactobacillus plantarum WCFS1 by two different polysaccharides isolated from Lactobacillus rhamnosus LOCK 0900," Appl Environ Microbiol, 80(20): 6506-6516 (2014). Epub Aug. 8, 2014.
Jiang, L. et al., "Polysaccharide isolated from seeds of Plantago asiatica L. induces maturation of dendritic cells through MAPK and NF-κB pathway," Saudi J Biol Sci. Sep. 2018; 25(6): 1202-1207. Epub Sep. 29, 2017.
Laino, J. et al., "Targeting of Immune Cells by Dual TLR2/7 Ligands Suppresses Features of Allergic Th2 Immune Responses in Mice," Journal of Immunological Research, vol. 2017, Article ID 7983217 (2017), 13 pages.
Li, X. et al., "Polysaccharide purified from Polyporus umbellatus (Per) Fr induces the activation and maturation of murine bone-derived dendritic cells via toll-like receptor 4," Cellular Immunology, 265(1): 50-56 (2010). Epub Jul. 14, 2010.
Park, S.-K. et al., "Acidic polysaccharides isolated from Phellinus linteus induce phenotypic and functional maturation of murine dendritic cells," Biochemical and Biophysical Research Communications, 312(2): 449-458 (Dec. 12, 2003).

\* cited by examiner

*Primary Examiner* — David W Berke-Schlessel
(74) *Attorney, Agent, or Firm* — COOLEY LLP; Cynthia Kozakiewicz; Robert E. Powers

(57) ABSTRACT

Bone marrow containers are described herein. Separation systems for separating activated immune cells from other components are described herein. Methods of activating an immune cell are described herein.

10 Claims, 4 Drawing Sheets

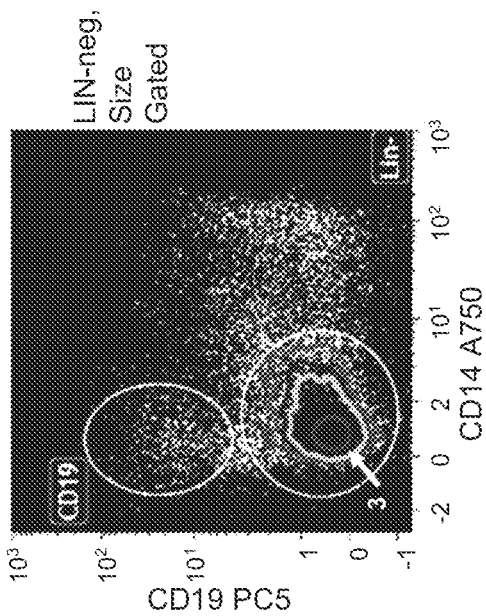
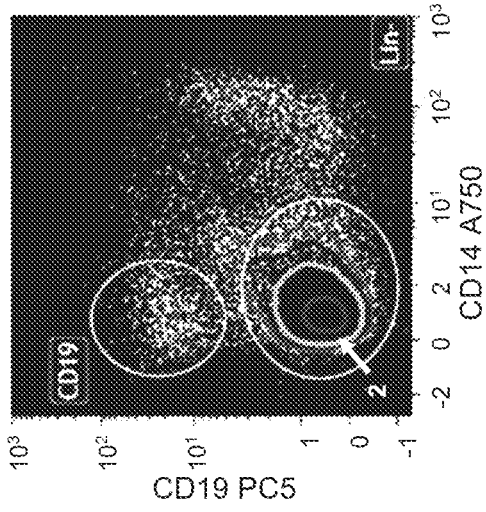
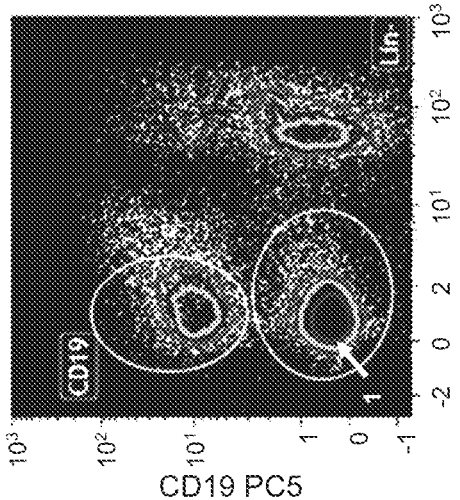
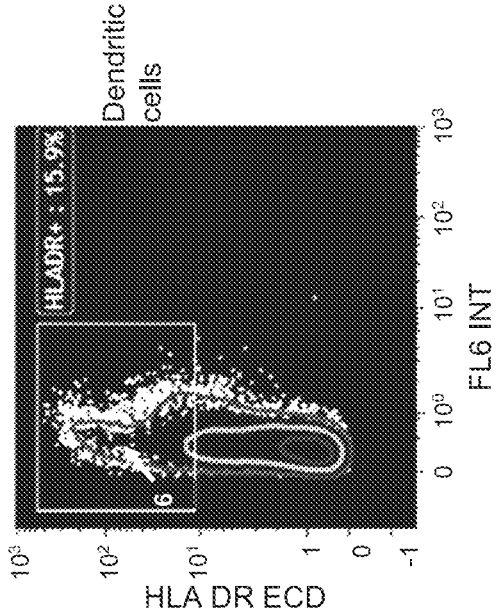
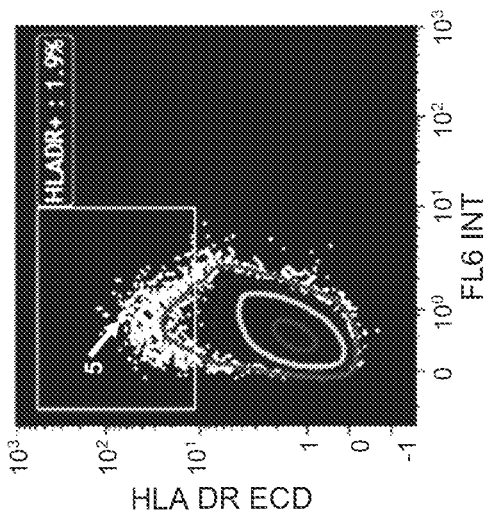
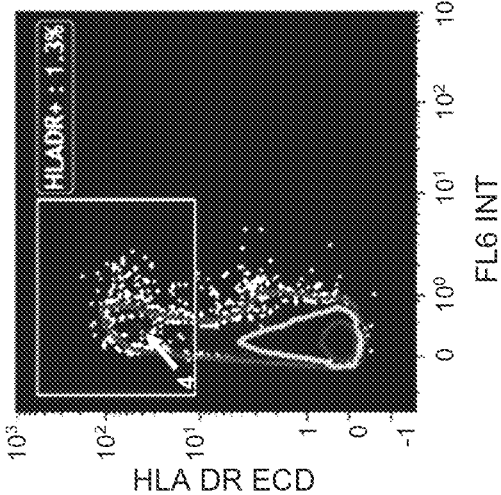

PB BM MNC

SIZE / VIABLE / SINGLETS

Gating Scheme

ACTIVATION OF IMMUNE CELLS

INCORPORATION BY REFERENCE TO ANY PRIORITY APPLICATIONS

This application claims the benefit as a divisional of U.S. patent application Ser. No. 16/160,006 filed on Oct. 15, 2018, which in turn claims the benefit as a nonprovisional application of U.S. Provisional Application No. 62/691775, filed Jun. 29, 2018. The foregoing provisional applications are hereby incorporated by reference in their entireties. Any and all applications for which a foreign or domestic priority claim is identified in the Application Data Sheet as filed with the present application are hereby incorporated by reference under 37 CFR 1.57.

BACKGROUND

Bone marrow has been used as an easily-accessed source of hematopoietic stem cells (HSCs) and other regenerative cell types such as mesenchymal stromal/stem cells (MSCs). Since the bone marrow is a renewing tissue, it can provide a useful source of renewable cells for regenerative medicine applications, particularly those where autologous cells are preferred.

Conventionally, bone marrow aspirates have been processed by separating cellular components. These methods can de-bulk the marrow by separating out erythrocytes (RBCs), which are conventionally regarded as having no value, and potentially even detrimental in regenerative medicine applications. In general, these methods of separation have exploited different physical characteristics of RBCs to enrich in the mononuclear cell fraction which contains the HSCs and MSCs.

Field

Some embodiments herein relate generally to methods, compositions, and manufactures for the activation of immune cells. In some embodiments, a composition comprising non-ionic hydrophilic branched polysaccharides and a Toll-like Receptor 2 (TLR2) ligand is used to activate bone marrow-derived myeloid cells.

SUMMARY

In some embodiments, a bone marrow container is described. The bone marrow container can comprise a composition comprising a non-ionic hydrophilic branched polysaccharide at a density, in which, if the composition is contacted with whole blood and centrifuged, the density is sufficient to permit fluid movement of whole blood through the non-ionic hydrophilic branched polysaccharide without separation of erythrocytes. The non-ionic hydrophilic branched polysaccharide can have a molecular weight greater than 20 kDa. The composition can comprise a TLR2 ligand. The composition can be contained within the container. The container can be sterile. In some embodiments, the non-ionic hydrophilic branched polysaccharide has a molecular weight of at least 70 kDa. In some embodiments, the non-ionic hydrophilic branched polysaccharide comprises poly(sucrose-co-epichlorhydrin). In some embodiments, the non-ionic hydrophilic branched polysaccharide has a density less than 1 gram per liter. In some embodiments, the TLR2 ligand is selected from the group consisting of hyaluronon, hyaluronic acid, monosodium urate crystals, biglycan, endoplasmin, HMGB1, HSP60, HSP70, human cardiac myosin, zymosan, lipoteichoic acids, peptidoglycans including Pam2CSK4, Pam3CSK4, lipoproteins from plasma, and lipopolysaccharide (LPS). In some embodiments, the non-ionic hydrophilic branched polysaccharide comprises, consists essentially of, or consists of poly(sucrose-co-epichlorhydrin) at a density of less than 1 gram per liter, and wherein the TLR2 ligand comprises, consists essentially of, or consists of hyaluronic acid. In some embodiments, the container is selected from the group consisting of a bag, a vacutainer, and a syringe. In some embodiments, the bone marrow container further comprises an integral delivery device. In some embodiments, the bone marrow container further comprises an activation/sedimentation solution. In some embodiments, the bone marrow container further comprises dextran and/or hes. In some embodiments, the dextran is at a concentration of at least about 4%. In some embodiments, the bone marrow container further comprises a volume configured to receive bone marrow, wherein, when bone marrow is present in the volume, the concentration of the dextran in the bone marrow and the composition is at least about 1%. In some embodiments, the bone marrow is configured to be received by a separation system as described herein.

In some embodiments, a separation system is described. The separation system can comprise a chassis comprising a cavity configured to receive a bone marrow container as described herein. The chassis can comprise a track. The system can comprise a shaft disposed on the track, in which the shaft is configured to move along the track, thus compressing the bone marrow container when the bone marrow container is disposed in the chassis. In some embodiments, the shaft is configured to compress the bone marrow container against an inner surface of the chassis. In some embodiments, the shaft is selected from the group consisting of a roller and a slider. In some embodiments, the shaft is configured to snap into position against a bone marrow container disposed in the chassis, thereby defining at least two portions of the bone marrow container.

In some embodiments, a kit is described. The kit can comprise a bone marrow container as described herein. The kit can further comprise a bone marrow aspiration needle such as a luer lock. In some embodiments, the kit further comprises a filter. The filter can have a pore size smaller than a diameter of a myeloid cell. In some embodiments, the pore size is less than or equal to 200 microns. In some embodiments, the kit further comprises an activation/sedimentation solution. In some embodiments, the kit further comprises a separation system as described herein.

In some embodiments, a method of activating immune cells of a subject is described. The methods can comprise obtaining bone marrow of the subject. The bone marrow can comprise immune cells. The method can comprise incubating the bone marrow with a non-ionic hydrophilic branched polysaccharide and a TLR2 ligand. The non-ionic hydrophilic branched polysaccharide can be at a density, such that, if the bone marrow is contacted with whole blood and centrifuged, the density is sufficient to permit fluid movement of whole blood through the non-ionic hydrophilic branched polysaccharide without separation of erythrocytes. The non-ionic hydrophilic branched polysaccharide can have a molecular weight greater than 20 kDa. The incubating can be performed until the immune cells are activated. For example, the incubation can be for at least 1, 2, 3, 4, 5, 6, 7, 8, 9, 10, 11, or 12 hours, including ranges between any two of the listed values. The method can further comprise administering the activated immune cells to the subject. In some embodiments, the method further comprises identifying a subject as being in need of immune cell activation. In some embodiments, the subject has cancer. In some embodiments, the incubating further comprises incubating the bone marrow with a cancer cell antigen. In some embodiments, the non-ionic hydrophilic branched polysaccharide has a molecular weight of at least 70 kDa. In some embodiments, the non-ionic hydrophilic branched polysaccharide comprises poly(sucrose-co-epichlorhydrin). In some embodiments, the non-ionic hydrophilic branched polysaccharide has a density less than 1 gram per liter. In some embodiments, the TLR2 ligand is selected from the group consisting of hyaluronon, hyaluronic acid, monosodium urate crystals, biglycan, endoplasmin, HMGB1, HSP60, HSP70, human cardiac myosin, zymosan, lipoteichoic acids, lipoproteins from plasma, LPS, and peptidoglycans including Pam2CSK4 and Pam3CSK4, and combinations of two or more of the listed items. In some embodiments, the non-ionic hydrophilic branched polysaccharide comprises, consists essentially of, or consists of poly(sucrose-co-epichlorhydrin) at a density of less than 1 gram per liter, and the TLR2 ligand comprises hyaluronic acid. In some embodiments, the non-ionic hydrophilic branched polysaccharide comprises, consists essentially of, or consists of poly(sucrose-co-epichlorhydrin) at a density of less than 1 gram per liter, and wherein the TLR2 ligand comprises, consists essentially of, or consists of hyaluronic acid. In some embodiments, the incubating is performed in a bone marrow container as described herein. In some embodiments, the method further comprises disposing the bone marrow container in the separation system as described herein, and snapping the shaft into position against the bone marrow container, thus defining two portions of the bone marrow container. The method can further comprise, after the incubating, moving the shaft along the track, thus compressing the contents of the bone marrow container, and extruding immune cells from the bone marrow. In some embodiments, the method further comprises incubating the bone marrow with an activation/sedimentation solution, thereby sedimenting red blood cells from the bone marrow. In some embodiments, the activated immune cells comprise, consist essentially of, or consist of myeloid cells. In some embodiments, the activated immune cells comprise CD11b$^+$ CD54$^+$ granuloyctes and/or CD66b+ neutrophils. In some embodiments, the method further comprises separating the activated immune cells from the non-ionic hydrophilic branched polysaccharide and the TLR2 ligand prior to administering the activated immune cells to the subject. In some embodiments, the activated immune cells are administered to a musculoskeletal tissue of the subject. In some embodiments, the method does not comprise leukaphoresis.

BRIEF DESCRIPTION OF THE DRAWINGS

FIGS. 1A-F are a series of graphs showing flow cytometric analysis of myeloid dendritic cell activation after exposure of bone marrow aspirate to FICOLL reagent and TLR2 ligands. FIG. 1A and FIG. 1D (peripheral blood sample positive control, PB), FIG. 1B and FIG. 1E (whole bone marrow negative control prior to exposure to Ficol and TLR2 agonists), and FIG. 1C and FIG. 1F (bone marrow aspirate mononuclear cells after exposure to Ficol and TLR2 agonists, MNC). Lineage negative, CD14 negative, myeloid size-gated classical dendritic cells (FIG. 1A, FIG. 1B, and FIG. 1C; white arrows denote dendritic cells in regions 1, 2, and 3) and gated dendritic cells were analyzed for activation by measuring the percentage of activated cells for HLA-DR expression by percentage positive and relative fluorescence intensity (FIG. 1D, FIG. 1E, and FIG. 1F).

DETAILED DESCRIPTION

Figure 2A:
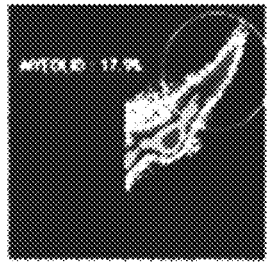
FIGS. 2A-I Flow cytometric gating scheme to isolate myeloid sized-cells by forward and orthogonal light scatter (FIG. 2A, 2B, and 2C), viability using dye-exclusion to discriminate live cells from dead (FIG. 2d, FIG. 2E, and FIG. 2F), and single-cells from doublets and debris using the proportion of signal area to signal width (FIG. 2G, FIG. 2H, and FIG. 2I).
Figure 2B:
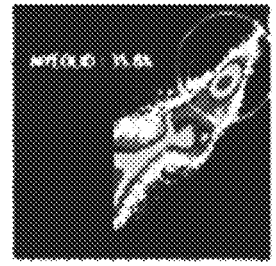
Figure 2C:
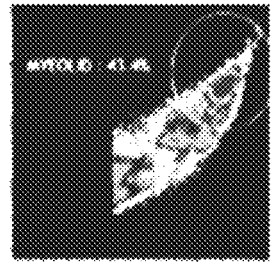
Figure 2D:
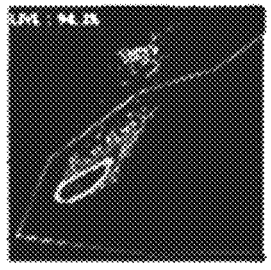
Figure 2E:
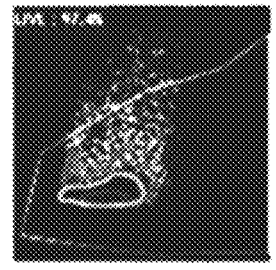
Figure 2F:
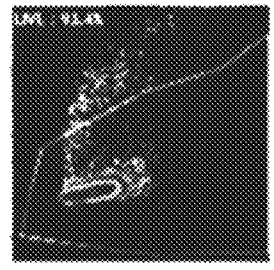

It is observed herein that a non-ionic hydrophilic branched polysaccharide such as poly(sucrose-co-epichlorhydrin), in combination with a TLR2 ligand (such as hyaluronic acid) can activate immune cells in bone marrow, such as regenerative cells. The activated immune cells can comprise, consist essentially of, or consist of myeloid lineage. Described in accordance with embodiments herein are bone marrow containers, compositions, methods, and kits comprising a non-ionic hydrophilic branched polysaccharides and a TLR2 ligand. The non-ionic hydrophilic branched polysaccharide can have a molecular weight of at least 20 kDa. The non-ionic hydrophilic branched polysaccharide can be at a density sufficient to permit the permit fluid movement of whole blood through the non-ionic hydrophilic branched polysaccharide without separation of erythrocytes. In contrast, conventional uses of non-ionic hydrophilic branched polysaccharides in blood processing typically would implement these polysaccharides at higher concentrations (greater than 1.0 g/l) for density-mediated separation of erythrocytes from the mononuclear fraction (e.g., under centrifugation). In some embodiments, the bone marrow container comprises the non-ionic hydrophilic branched polysaccharides and the TLR2 ligand. Bone marrow aspirates can be added to the container, and immune cells can be activated by incubating the bone marrow aspirates with the non-ionic hydrophilic branched polysaccharides and the TLR2 ligand in the container. In some embodiments, a method of activating immune cells comprises incubating bone marrow (such as bone marrow aspirate) with the non-ionic hydrophilic branched polysaccharides and a TLR2 ligand as described herein.

As used herein, "activating" an immune cell has its ordinary and customary meaning as would be understood by one of ordinary skill in the art in view of this disclosure. It refers to immune cell proliferation, maturation, mobilization (such as migration), metabolism or catabolism, and/or activity (such as cytokine, growth factor, and/or enzyme secretion).

Non-Ionic Hydrophilic Branched Polysaccharides

Bone marrow treatment containers, kits, and methods of some embodiments comprise non-ionic hydrophilic branched polysaccharides. Examples of suitable non-ionic hydrophilic branched polysaccharides include, but are not limited to, poly(sucrose-co-epichlorhydrin), which is commercially available as FICOLL polysaccharide. It is contemplated herein that large branched polysaccharides having a molecular weight of at least 20 kDa can activate the innate immune system. Without being limited by theory, it is contemplated that non-ionic hydrophilic branched polysaccharides having a suitably high molecular weight have a structure that mimics a bacterial cell wall. In some embodiments, the -ionic hydrophilic branched polysaccharide comprises more monomers than a disaccharide, for example at least a trisaccharide or greater. In some embodiments, the non-ionic hydrophilic branched polysaccharide has a density of at least 20 kDa, for example, at least 20 kDa, 30 kDa, 40 kDa, 50 kDa, 60 kDa, 70 kDA, 80 kDa, 90 kDa, 100 kDa, 150 kDa, 200 kDa,or 500 kDa, including ranges between any two of the listed values, for example, 20-500 kDa, 20-200 kDa, 20-100 kDa, 20-80 kDa, 50-500 kDa, 50-200 kDa, 50-100 kDa, 50-80 kDa, 70-500 kDa, 70-200 kDa, 70-100 kDa, and 70-80 kDa.

While non-ionic hydrophilic branched polysaccharides have conventionally been used at high densities for the separation of erythorcytes from blood (for example by centrifugation), it is contemplated herein that ionic hydrophilic branched polysaccharides can be useful for activating immune cells at much lower densities. In some embodiments, the non-ionic hydrophilic branched polysaccharide is at a density, so that, if contacted with whole blood and centrifuged, whole blood may move fluidly through the non-ionic hydrophilic branched polysaccharide without separation of erythrocytes. In some embodiments, the non-ionic hydrophilic branched polysaccharide is provided at a density of less than 1 gram per liter, for example less than 1 g/l, 0.99 g/l, 0.9 g/l, 0.8 g/l, 0.7 g/l, 0.6 g/7, 0.5 g/l, 0.4 g/l, 0.3 g/l, 0.2 g/l, 0.1 g/l, 0.05 g/l, $10^{-2}$ g/l, $2\times10^{-3}$ g/l, $10^{-3}$ g/l, $10^{-5}$ g/l, $2\times10^{-6}$ g/l, $10^{-6}$ g/l, $10^{-7}$ g/l, $10^{-8}$ g/l, $2\times10^{-9}$ g/l, or $10^{-9}$ g/l, including ranges between any two of the listed values, for example, $10^{-9}$-$10^{-6}$ g/l, $10^{-9}$-$10^{-3}$ g/l, $10^{-9}$-$10^{-2}$ g/l, $10^{-9}$-0.1 g/l, $10^{-9}$-0.5 g/l, $10^{-9}$-0.9 g/l, $10^{-9}$-0.09 g/l, $10^{-6}$-$10^{-3}$ g/l, $10^{-6}$-$10^{-2}$ g/l, $10^{-6}$-0.1 g/l, $10^{-6}$-0.5 g/l, $10^{-6}$-0.9 g/l, $10^{-6}$-0.09 g/l, $2\times10^{-6}$-$10^{-2}$ g/l, $2\times10^{-6}$-0.1 g/l, $2\times10^{-6}$-0.5 g/l, $2\times10^{-6}$-0.9 g/l, $2\times10^{-6}$-0.09 g/l, $10^{-3}$-$10^{-2}$ g/l, $10^{-3}$-0.1 g/l, $10^{-3}$-0.5 g/l, $10^{-3}$-0.9 g/l, $10^{-3}$-0.09 g/l, 0.002-0.01 g/l, 0.002-0.1 g/l, 0.002-0.5 g/l, 0.002-0.9 g/l, 0.002-0.09 g/l, 0.01 g/l-0.99 g/l, 0.01 g/l-0.9 g/l, 0.01 g/l-0.5 g/l, 0.01 g/l-0.2 g/l, 0.01 g/l-0.1 g/l, 0.1 g/l-0.99 g/l, 0.1 g/l-0.9 g/l, 0.1 g/l-0.5 g/l, 0.1 g/l-0.2 g/l, 0.5 g/l-0.99 g/l, 0.5 g/l-0.9 g/l, and 0.5 g/l-0.7 g/l.

TLR2 Ligands

TLR2 ligands can activate myeloid cells. Without being limited by theory, it is contemplated that TLR2 ligands can activate myeloid cells to improve their therapeutic effectiveness. Accordingly, bone marrow treatment containers, kits, compositions, and methods of some embodiments comprise TLR2 ligands. Examples of suitable TLR2 ligands for methods, compositions, bone marrow containers, and kits of some embodiments herein include, but are not limited to, hyaluronon, hyaluronic acid, monosodium urate crystals, biglycan, endoplasmin, HMGB1, HSP60, HSP70, human cardiac myosin, zymosan, lipoteichoic acids, lipoproteins from plasma, LPS, peptidoglycans including Pam2CSK4, Pam3CSK4, and combinations of two or more of the listed items. In some embodiments, the TLR2 ligand comprises, consists essentially of, or consists of hyaluronic acid. In bone marrow treatment containers, kits, compositions, and methods of some embodiments, the TLR2 ligand is at a concentration of at least 1 µg/ml, for example at least 1, 2, 3, 4, 5, 6, 7, 8, 9, 10, 50, 100 or 500 µg/ml, or at least 1 mg/ml, for example 1, 2, 3, 4, 5, 6, 7, 8, 9, or 10 mg/ml, including ranges between any two of the listed values, for example, 1-10 µg/ml, 1-100 µg/ml, 1 µg/ml-1 mg/ml, 1 µg/ml-10 mg/ml, 10-100 µg/ml, 10 µg/ml-1 mg/ml, 10 µg/ml-10 mg/ml, 100 µg/ml-1 mg/ml, 100 µg/ml-10 mg/ml, or 1-10 mg/ml.

Activation/Sedimentation Solutions

Some embodiments include activation/sedimentation solutions. The activation/sedimentation solutions can sediment erythrocytes from bone marrow, thus debulking the bone marrow and increasing the concentration of activated immune cells. Dextran and/or hydroxyethyl starch (hes) can sediment erythrocytes. Accordingly, in some embodiments, the activation/sedimentation solution comprises, consists essentially of, or consists of dextran and/or hes. In some embodiments, the activation/sedimentation solution comprises, consists essentially of, or consists of hes. In some embodiments, the activation/sedimentation solution comprises, consists essentially of, or consists of dextran. In some embodiments, the dextran and/or hes is at a concentration so that, upon addition of bone marrow, the concentration of dextran and/or hes is at least 1%, for example, at least 1%, 2%, 3%, or 4%, including ranges between any two of the listed values, for example 1-4%, 1-3%, 1-2%, 2-3%, 2-4%, or 3-4%. The activation/sedimentation solution can be suitable for incubating with bone marrow and the composition (comprising non-ionic hydrophilic branched polysaccharide and TLR2 ligand) in the bone marrow container, so as to sediment erythrocytes, thus debulking the activated immune cells. In some embodiments, the dextran and/or hes has a high molecular weight. In some embodiments, the dextran and/or hes is of a 510(k)-compatible grade.

In some embodiments, the activation/sedimentation solution is separate from the composition comprising non-ionic hydrophilic branched polysaccharide and TLR2 ligand. For example, the activation/sedimentation solution can be separate from the bone marrow container as described herein, and can be added to the container later. In some embodiments, the activation/sedimentation solution is part of a composition comprising non-ionic hydrophilic branched polysaccharide and TLR2 ligand as described herein.

Compositions

In some embodiments, a composition comprises a non-ionic hydrophilic branched polysaccharide as described herein and a TLR2 ligand as described herein. The non-ionic hydrophilic branched polysaccharide can have a molecular weight of at least 20 kDa as described herein. The non-ionic hydrophilic branched polysaccharide can have a density of no more than 1 g/liter as described herein. The composition can be sterile. In some embodiments, the non-ionic hydrophilic branched polysaccharide comprises, consists essentially of, or consists of comprises poly(sucrose-co-epichlorhydrin). In some embodiments TLR2 ligand comprises, consists essentially of, or consists of hyaluronic acid. In some embodiments, the composition is comprises in a solution (the solution can comprise, consist essentially of, or consist of the composition), such as an aqueous solution. In some embodiments, the composition is a solution, such as an aqueous solution. In some embodiments, the non-ionic hydrophilic branched polysaccharide is provided at a density of less than 1 gram per liter, for example less than 1 g/l, 0.99 g/l, 0.9 g/l, 0.8 g/l, 0.7 g/l, 0.6 g/7, 0.5 g/l, 0.4 g/l, 0.3 g/l, 0.2 g/l, 0.1 g/l, 0.05 g/l, $10^{-2}$ g/l, $2\times10^{-3}$ g/l, $10^{-3}$ g/l, $10^{-5}$ g/l, $2\times10^{-6}$ g/l, $10^{-6}$ g/l, $10^{-7}$ g/l, $10^{-8}$ g/l, $2\times10^{-9}$ g/l, or $10^{-9}$ g/l, including ranges between any two of the listed values, for example, $10^{-9}$-$10^{-6}$ g/l, $10^{-9}$-$10^{-3}$ g/l, $10^{-9}$-$10^{-2}$ g/l, $10^{-9}$-0.1 g/l, $10^{-9}$-0.5 g/l, $10^{-9}$-0.9 g/l, $10^{-9}$-0.09 g/l, $10^{-6}$-$10^{-3}$ g/l, $10^{-6}$-$10^{-2}$ g/l, $10^{-6}$-0.1 g/l, $10^{-6}$-0.5 g/l, $10^{-6}$-0.9 g/l, $10^{-6}$-0.09 g/l, $2\times10^{-6}$-$10^{-2}$ g/l, $2\times10^{-6}$-0.1 g/l, $2\times10^{-6}$-0.5 g/l, $2\times10^{-6}$-0.9 g/l, $2\times10^{-6}$-0.09 g/l, $10^{-3}$-$10^{-2}$ g/l, $10^{-3}$-0.1 g/l, $10^{-3}$-0.5 g/l, $10^{-3}$-0.9 g/l, $10^{-3}$-0.09 g/l, 0.002-0.01 g/l, 0.002-0.1 g/l, 0.002-0.5 g/l, 0.002-0.9 g/l, 0.002-0.09 g/l, 0.01 g/l-0.99 g/l, 0.01 g/l-0.9 g/l, 0.01 g/l-0.5 g/l, 0.01 g/l-0.2 g/l, 0.01 g/l-0.1 g/l, 0.1 g/l-0.99 g/l, 0.1 g/l-0.9 g/l, 0.1 g/l-0.5 g/l, 0.1 g/l-0.2 g/l, 0.5 g/l-0.99 g/l, 0.5 g/l-0.9 g/l, and 0.5 g/l-0.7 g/l. In some embodiments, the TLR ligand is at a concentration of at least 1 µg/ml as described herein, for example at least 1, 2, 3, 4, 5, 6, 7, 8, 9, 10, 50, 100 or 500 µg/ml, or at least 1 mg/ml, for example 1, 2, 3, 4, 5, 6, 7, 8, 9, or 10 mg/ml, including ranges between any two of the listed values, for example, 1-10 µg/ml, 1-100 µg/ml, 1 µg/ml-1 mg/ml, 1 µg/ml-10 mg/ml, 10-100 µg/ml, 10 µg/ml-1 mg/ml, 10 µg/ml-10 mg/ml, 100 µg/ml-1 mg/ml, 100 µg/ml-10 mg/ml, or 1-10 mg/ml.

Without being limited by theory, it is contemplated that the non-ionic hydrophilic branched polysaccharide can activate an innate immune response, and that the TLR2 ligand can activate myeloid cells. In some embodiments, the composition comprises an amount of non-ionic hydrophilic branched polysaccharide sufficient to activate an innate immune response. In some embodiments, the composition comprises an amount of TLR2 ligand sufficient to activate myeloid cells. In some embodiments, the composition comprises an amount of non-ionic hydrophilic branched polysaccharide and a TLR2 ligand sufficient to activate myeloid cells and stimulate an innate immune response. In some embodiments, the composition comprises an amount of non-ionic hydrophilic branched polysaccharide and a TLR2 ligand sufficient to activate CD66b+ neutrophils.

In some embodiments, the composition further comprises an activation/sedimentation solution as described herein.

In some embodiments, the composition is for use in activating immune cells as described herein, for example, immune cells of the myeloid lineage. In some embodiments, the use is an in vitro use.

Bone Marrow Containers

It is contemplated that a bone marrow container comprising a non-ionic hydrophilic branched polysaccharide and a TLR2 ligand as described herein can activate immune cells of bone marrow. The bone marrow container can be useful for stimulating immune response in autologous bone marrow of a patient in need of an immune response, and/or for hydrating an implantable gel or putty (such as Demineralized Bone Matrix (DBM)) prior to implantation. Accordingly, in some embodiments, a bone marrow container is described. The bone marrow container can contain a composition comprising a non-ionic hydrophilic branched polysaccharide as described herein and a TLR2 ligand as described herein. The ionic hydrophilic branched polysaccharide can be at a density, in which, if the composition is contacted with whole blood and centrifuged, the density permits fluid movement of whole blood through the non-ionic hydrophilic branched polysaccharide without separation of erythrocytes. The reference centrifugation parameters can be, for example at least 50 g, for example at least 100 g, 200 g, 300 g, or 400 g. The non-ionic hydrophilic branched polysaccharide can have a molecular weight greater than 20 kDa as described herein, for example at least at least 20 kDa, 30 kDa, 40 kDa, 50 kDa, 60 kDa, 70 kDA, 80 kDa, 90 kDa, 100 kDa, 150 kDa, 200 kDa,or 500 kDa, including ranges between any two of the listed values, such as 20-50 kDa, 20-100 kDa, 20-200 kDa, 20-500 kDa, 50-100 kDa, 50-200 kDa, 50-500 kDa, 70-100 kDa, 70-200 kDa, 70-500 kDa, 100-200 kDa, or 100-500 kDa,. The composition can be contained in the bone marrow container. The bone marrow container can be sterile. In some embodiments, the bone marrow container is configured for insertion into a separation system as described herein. In some embodiments, the non-ionic hydrophilic branched polysaccharide is at a density of less than 1 gram per liter. In some embodiments, the non-ionic hydrophilic branched polysaccharide comprises poly(sucrose-co-epichlorhydrin) at a density of less than 1 gram per liter, and the TLR2 ligand comprises hyaluronic acid.

Figure 3A:
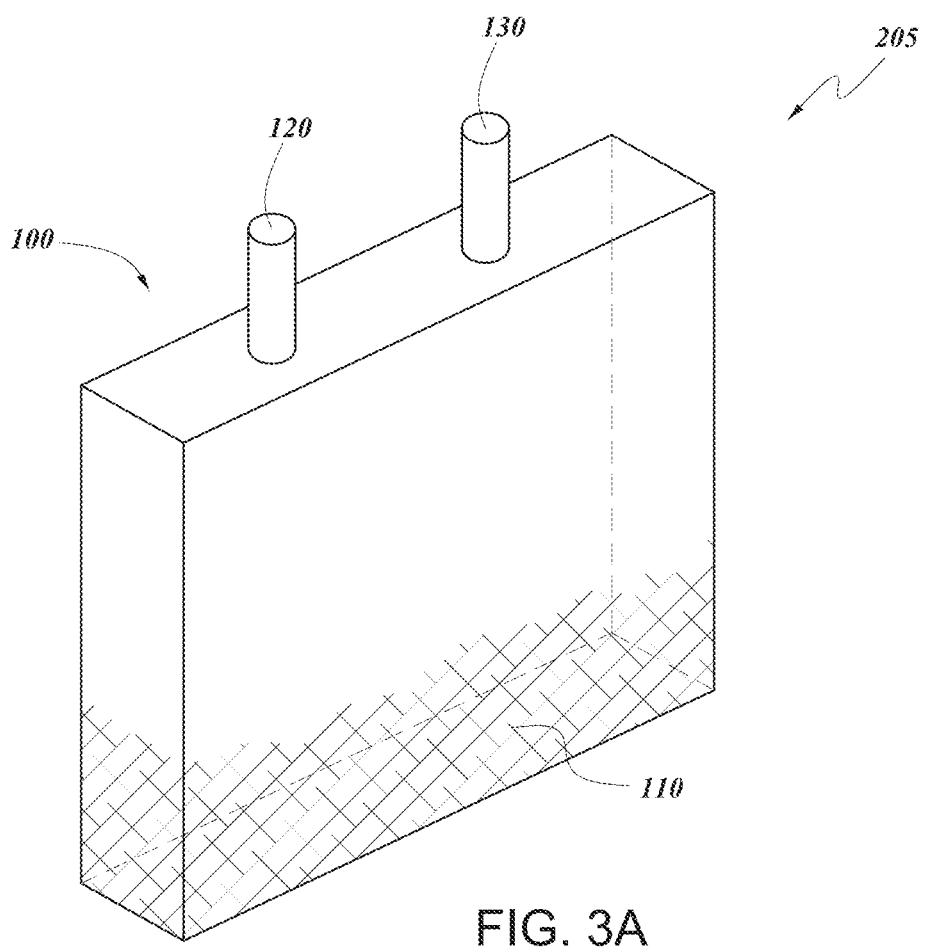
FIG. 3A is a diagram of a bone marrow container according to some embodiments herein.

An example bone marrow container of some embodiments is depicted in FIG. 3A. The bone marrow container 100 can contain a composition comprising, consisting essentially of, or consisting of a non-ionic hydrophilic branched polysaccharides and a TLR2 ligand 110 as described herein. The composition 110 can be disposed in an interior of the bone marrow container 110. The interior of the bone marrow container can be sterile. The bone marrow container 100 can further comprise an inlet 120 and an outlet 130. The inlet and the outlet can place the interior of the bone marrow container 100 in fluid communication with the exterior. In some embodiments, the inlet 120 comprises a channel and/or valve. In some embodiments the inlet 120 is sealable, for example by pressure, friction, or adhesive. In some embodiments, the outlet 130 comprises a channel and/or valve. In some embodiments, the outlet 130 is sealable, for example by pressure, friction, or adhesive. In some embodiments, the inlet 120 and the outlet 130 are the same structure. In some embodiments, the inlet 120 and the outlet 130 are seperate structures. In some embodiments, the bone marrow container 100 further comprises an integral delivery device (not shown), such as an intravenous needle. The integral delivery device can be in fluid communication with the outlet 130, and can be configured to administer activated immune cells from the container to a subject in need thereof.

In some embodiments, the bone marrow container is selected from the group consisting of a bag, a vacutainer, and a syringe. In accordance with some embodiments, after bone marrow is incubated in the bone marrow container so as to activate immune cells as described herein, the activated immune cells are administered to a subject in need thereof. The immune cells can be autologous. Accordingly, in some embodiments, the bone marrow container further comprises a delivery device, for example a needle such as an intravenous needle. In some embodiments, the delivery device is integral to the bone marrow container. In some embodiments, the delivery device is configured to be attached to, and optionally detached from, the bone marrow container. For example, the delivery device can be configured to be placed in fluid communication with an outlet of the bone marrow container.

In some embodiments, the bone marrow container is configured to receive a volume of 2-4 ml per draw, up to about 25 ml per draw. Thus, the bone marrow container can have a volume to accommodate the drawn bone marrow and the composition comprising the non-ionic hydrophilic branched polysaccharide and TLR2 ligand. Accordingly, in some embodiments, the bone marrow container has a volume of at least 2, 5, 10, 15, 20, 25, 30, 35, 40, 45, 50, 60, 70, 80, 90, or 100 ml, including ranges between any two of the listed values, for example 2-25 ml, 2-30 ml, 2-40 ml, 2-50 ml, 2-70 ml, 2-100 ml, 5-25 ml, 5-30 ml, 5-40 ml, 5-50 ml, 5-70 ml, 5-100 ml, 10-25 ml, 10-30 ml, 10-40 ml, 10-50 ml, 10-70 ml, 10-100 ml, 20-25 ml, 20-30 ml, 20-40 ml, 20-50 ml, 20-70 ml, 20-100 ml, 50-70 ml, or 50-100 ml.

It can be advantageous to remove some or all erythrocytes from bone marrow comprising activated immune cells as described herein, for example to de-bulk the bone marrow, and to increase the concentration of activated mononuclear immune cells in the bone marrow. In some embodiments, the bone marrow container is further configured for sedimentation of erythrocytes. Accordingly, in some embodiments, the bone marrow container comprises an activation/sedimentation solution as described herein. The activation/sedimentation solution can comprise dextran and/or hes. In some embodiments, the bone marrow container comprises a volume configured to receive bone marrow, and when bone marrow is present in the volume, the concentration of the dextran and/or hes in the bone marrow and activation/sedimentation solution combined is at least about 1%.

In some embodiments, the bone marrow container is a point of care device. As such, in some embodiments, the bone marrow container is portable.

Separation Systems

Separation systems can be useful in conjunction with bone marrow containers as described herein to prepare concentrated activated immune cells after bone marrow has been incubated in the bone marrow container.

Figure 3B:
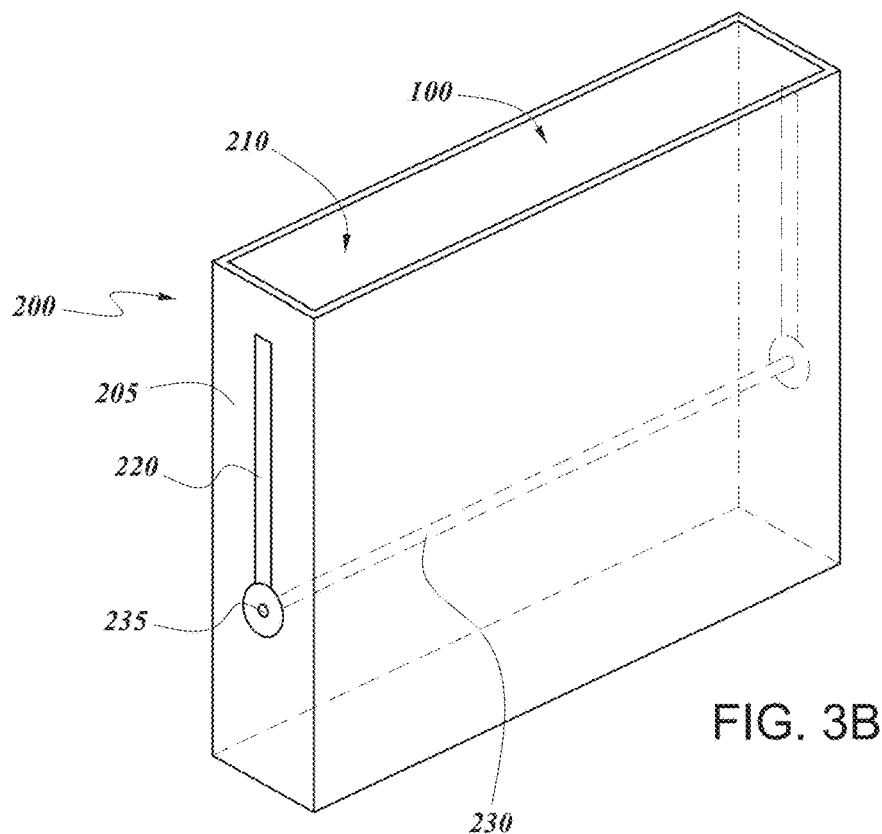
FIGS. 3B-C are diagrams of a separation system according to some embodiments herein. The separation system can be configured to receive the bone marrow container as described herein.
Figure 3C:
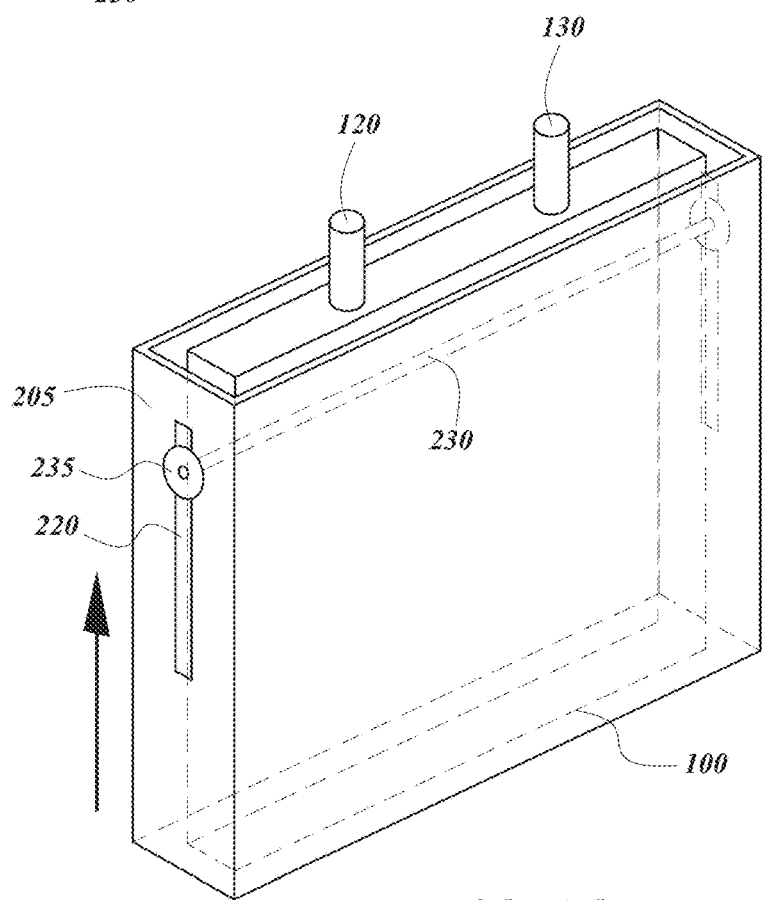

An example separation system of some embodiments is depicted in FIGS. 3B and 3C. FIG. 3B depicts a separation system 200 in a first configuration (prior to separation of bone marrow in a bone marrow container 100). FIG. 3C depicts a separation system 200 in a second configuration (after separation of the bone marrow in the bone marrow container 100).

With reference to FIG. 3B, the separation system 200 is configured to receive a bone marrow container 100 as described herein. The separation system 200 can comprise a chassis 205 comprising a cavity 210 configured to contain the bone marrow container 100. The chassis 205 can further comprise a track 220. The track 220 can be disposed along an axis of the cavity 210. A shaft 230 can be disposed on the track. Optionally, the shaft 230 is in mechanical communication with a handle 235, so that the shaft 230 can be moved along the track 220 via the handle 235. As such, as the shaft 230 is moved along the track 220, the shaft 230 can pass through the cavity. In some embodiments, the shaft 230 is selected from the group consisting of a roller and a slider. In some embodiments, the shaft 230 is configured to snap into position against a bone marrow container 100 disposed in the chassis 205, thus defining at least two portions of the bone marrow container 100. In some embodiments, the shaft 230 is configured to compress the bone marrow container 100 against an inner surface of the chassis 205. In some embodiments, the separation system 200 comprises a cavity 210 configured to receive the bone marrow container 100 as described herein, the chassis comprising a track 220. The separation system further comprises a shaft 230 disposed on the track 220, in which the shaft 230 is configured to move along the track 220, thus compressing the bone marrow container 100 when the bone marrow container 100 is disposed in the chassis 205. In some embodiments, the chassis 205 is plastic.

With reference to FIG. 3C, when the bone marrow container 100 is disposed within the cavity 220, the inlet 120 and outlet 130 can remain accessible. As the shaft 230 moves along the track 220, and passes through the cavity 210, the shaft 230 can compress the bone marrow container 100 therein. The movement of the shaft 230 along the track toward the outlet 130 can extrude activated immune cells from the bone marrow container 100 through the outlet 130. In some embodiments, an activation/sedimentation solution (which can comprise, consist essentially of, or consist of dextran and/or hes) can be added through the inlet 120 and mixed with the composition 110 and incubated, permitting activation of immune cells as described herein and also sedimentation of other components, such as erythrocytes. The shaft 230 can then be moved along the track 220, for example by pulling the handle, thus compressing the bone marrow container 100 and extruding activated immune cells through the outlet 130. In some embodiments, the incubation is for at least 0.5 hours, 1 hour, 1.5 hours, or 2 hours.

Kits

In some embodiments, a kit is described. The kit can comprise a bone marrow container as described herein. The bone marrow container can comprise a composition comprising a non-ionic hydrophilic branched polysaccharide as described herein and a TLR2 ligand as described herein. The kit can further comprise a bone aspiration needle, for example a luer lock. The bone aspiration needle can be suitable for administering bone marrow aspirate through the inlet of the bone marrow container.

In some embodiments, the kit further comprises a filter. The filer can be suitable for separating myeloid cells from other components of bone marrow. As such, in some embodiments, the filter has a pore size smaller than the diameter of a myeloid cell. In some embodiments, the filter has pore size is less than or equal to 200 microns, 150 microns, 100 microns, or 50 microns, including ranges between any two of the listed values, for example 50-200 microns, 50-150 microns, or 100-200 microns. In some embodiments, the filter can be used to retain myeloid cells, while disposing of smaller components of the bone marrow container and bone marrow (for example, the filter can be disposed in a fluid path comprising the interior of the bone marrow container and the outlet, so that substances smaller than myeloid cells can be expelled through the outlet while myeloid cells are retained).

In some embodiments, the kit further comprises an activation/sedimentation solution. In some embodiments, the activation/sedimentation solution is disposed inside the bone marrow container of the kit. In some embodiments, the activation/sedimentation solution is disposed separately from the bone marrow container, for example in a separate container. Dry and/or lyophilized precursors to activation/sedimentation solutions can also suitably be reconstituted as activation/sedimentation solutions upon the addition of a suitable fluid, for example bone marrow. Thus, while activation/sedimentation "solutions" are referred to herein as a shorthand, it will also be understood that suitable dry and/or lyophilized precursors are also contemplated.

In some embodiments, the kit further comprises plasmin. The plasmin can be useful for clotting and delivery of activated immune cells.

In some embodiments, the kit further comprises a separation system as described herein.

Methods of Activating Immune Cells

Some embodiments include methods of activating immune cells of a subject. The method can comprise obtaining bone marrow of the subject. The bone marrow can comprise immune cells. The method can comprise incubating the bone marrow with a composition comprising a non-ionic hydrophilic branched polysaccharide and a TLR2 ligand, for example a composition comprising a non-ionic hydrophilic branched polysaccharide and a TLR2 ligand as described herein. The non-ionic hydrophilic branched polysaccharide can have a molecular weight greater than 20 kDa. The non-ionic hydrophilic branched polysaccharide can be at a density, so that if the bone marrow is contacted with whole blood and centrifuged, the density is sufficient to permit fluid movement of whole blood through the non-ionic hydrophilic branched polysaccharide without separation of erythrocytes. The incubating can be performed until the immune cells are activated. For example, the incubation can be for at least 1, 2, 3, 4, 5, 6, 7, 8, 9, 10, 11, or 12 hours, including ranges between any two of the listed values. For example, it has been shown that incubating bone marrow overnight with a non-ionic hydrophilic branched polysaccharide and a TLR2 ligand in accordance with some embodiments can activate immune cells (See Example 1). The method can comprise administering the activated immune cells to the subject. As such, the method of some embodiments delivers autologous activated immune cells to the subject. In some embodiments, the density of the non-ionic hydrophilic branched polysaccharide is no more than 1 g/liter. In some embodiments, the non-ionic hydrophilic branched polysaccharide and TLR2 ligand are disposed in a bone marrow container as described herein, and the incubating is performed in the bone marrow container. In some embodiments, the activated immune cells comprise, consist essentially of, or consist of myeloid cells. In some embodiments, the activated immune cells comprise, consist essentially of, or consist of CD66b+ neutrophils. In some embodiments, the bone marrow (and the activated immune cells) are autologous to the subject. In some embodiments, the bone marrow (and activated immune cells) are allogenic, for example if the patient is deficient in bone marrow and/or immune cell production and/or activity.

In some embodiments, the method further comprises identifying a subject as being in need of immune cell activation. In some embodiments, the subject has cancer. It is contemplated that activating immune cells in a cancer patient can be useful for mounting an immune response against the cancer. Moreover, it is contemplated that activating immune cells in the presence of a cancer cell antigen can activate an immune response targeting that tumor cells. As such, in some embodiments, the method comprises identifying the subject as having cancer. The method can further comprise incubating the bone marrow with a cancer cell antigen, for example a cancer cell antigen that is present on a tumor cell of the subject's cancer. The incubating can be in a bone marrow container as described herein. In some embodiments, the cancer cell antigen is comprised by a composition that also comprises the non-ionic hydrophilic branched polysaccharide and the TLR2 ligand. The activated immune cells can then be administered to the subject having cancer. In some embodiments, the activated immune cells are administered to a musculoskeletal tissue of the subject.

In the method of some embodiments, the non-ionic hydrophilic branched polysaccharide has a molecular weight of at least 20 kDa, 30 kDa, 40 kDa, 50 kDa, 60 kDa, 70 kDa, 80 kDa, 90 kDa, or 100 kDa, including ranges between any two of the listed values. In some embodiments, non-ionic hydrophilic branched polysaccharide comprises, consists essentially of, or consists of poly(sucrose-co-epichlorhydrin). In some embodiments, non-ionic hydrophilic branched polysaccharide comprises, consists essentially of, or consists of FICOLL polysaccharide. In the method of some embodiments, the non-ionic hydrophilic branched polysaccharide has a density less than 1 gram per liter, for example less than 1 gram per liter, for example less than 1 g/l, 0.99 g/l, 0.9 g/l, 0.8 g/l, 0.7 g/l, 0.6 g/7, 0.5 g/l, 0.4 g/l, 0.3 g/l, 0.2 g/l, 0.1 g/l, 0.05 g/l, $10^{-2}$ g/l, $10^{-3}$ g/l, $10^{-5}$ g/l, $10^{-6}$ g/l, $10^{-7}$ g/l, $10^{-8}$ g/l, $10^{-9}$ g/l, including ranges between any two of the listed values, for example, $10^{-9}$-$10^{-6}$ g/l, $10^{-9}$-$10^{-3}$ g/l, $10^{-9}$-$10^{-2}$ g/l, $10^{-9}$-0.1 g/l, $10^{-9}$-0.5 g/l, $10^{-9}$-0.9 g/l, $10^{-9}$-0.09 g/l, $10^{-3}$-$10^{-3}$ g/l, $10^{-6}$-$10^{-2}$ g/l, $10^{-6}$-0.1 g/l, $10^{-6}$-0.5 g/l, $10^{-6}$-0.9 g/l, $10^{-6}$-0.09 g/l, $10^{-3}$-$10^{-2}$ g/l, $10^{-3}$-0.1 g/l, $10^{-3}$-0.5 g/l, $10^{-3}$-0.9 g/l, $10^{-3}$-0.09 g/l, 0.01 g/l-0.99 g/l, 0.01 g/l-0.9 g/l, 0.01 g/l-0.5 g/l, 0.01 g/l-0.2 g/l, 0.01 g/l-0.1 g/l, 0.1 g/l-0.99 g/l, 0.1 g/l-0.9 g/l, 0.1 g/l-0.5 g/l, 0.1 g/l-0.2 g/l, 0.5 g/l-0.99 g/l, 0.5 g/l-0.9 g/l, and 0.5 g/l-0.7 g/l.

In the method of some embodiments, the TLR2 ligand is selected from the group consisting of hyaluronon, hyaluronic acid, monosodium urate crystals, biglycan, endoplasmin, HMGB1, HSP60, HSP70, human cardiac myosin, zymosan, lipoproteins from plasma, LPS, lipoteichoic acids, and peptidoglycans including Pam2CSK4 and Pam3CSK4, and combinations of two or more of the listed items.

In the method of some embodiments, the non-ionic hydrophilic branched polysaccharide comprises poly(sucrose-co-epichlorhydrin), and the TLR2 ligand comprises hyaluronic acid. In the method of some embodiments, the non-ionic hydrophilic branched polysaccharide comprises poly(sucrose-co-epichlorhydrin) at a density of less than 1 gram per liter, and the TLR2 ligand comprises hyaluronic acid.

In some embodiments, the incubating is performed in the bone marrow container as described herein. In some embodiments, the incubating is for at least 0.5 hours, 1 hour, 1.5 hours, 2 hours, or 3 hours, including ranges between any two of the listed values, for example, 0.5-1, 0.5-2, 0.5-3, 1-2, 1-3, 1.5-2, 1.5-3, or 2-3 hours.

In some embodiments, the method further comprises disposing the bone marrow container in the separation system as described herein. The method can further comprise snapping the shaft into position against the bone marrow container, thus defining two portions of the bone marrow container. After the incubating, the method can comprise, moving the shaft along the track, thus compressing the contents of the bone marrow container, and extruding immune cells from the bone marrow. In some embodiments, the immune cells are extruded through an outlet of the bone marrow container. The extruded immune cells can then be administered to a subject in need thereof.

In some embodiments, the method further comprises contacting the bone marrow with an activation/sedimentation solution, thus sedimenting red blood cells from the bone marrow. The activation/sedimentation solution can comprise, consist essentially of, or consist of dextran and/or hes, as described herein. In some embodiments, the incubating is performed in a bone marrow container as described herein, and the activation/sedimentation solution is present in the bone marrow container at the time that the bone marrow is placed in the bone marrow container. In some embodiments, the incubating is performed in a bone marrow container as described herein, and the activation/sedimentation solution is added to the bone marrow container, either at the same time as the bone marrow aspirate, or after the bone marrow aspirate is placed in thr container.

In some embodiments, the activated immune cells of the bone marrow comprise, consist essentially of, or consist of myeloid cells, such as CD11b+ CD54+ granuloyctes and/or CD66b+ neutorphils. In some embodiments, the activated immune cells comprise, consist essentially of, or consist of CD11b+ CD54+ granuloyctes. In some embodiments, the activated immune cells comprise, consist essentially of, or consist of CD66b+ neutrophils. In some embodiments, the activated immune cells comprise, consist essentially of, or consist of CD11b+ CD54+ granuloyctes and CD66b+ neutrophils.

In some embodiments, the method further comprising separating the activated immune cells from the non-ionic hydrophilic branched polysaccharide and the TLR2 ligand prior to administering the activated immune cells to the subject. In some embodiments, the separation is via filtration. In some embodiments, the separation is via a separation system as described herein.

In some embodiments, the method does not comprise leukophoresis.

Additional Embodiments

In addition to the items noted above, the following options are set forth:

1. A bone marrow container comprising: a composition comprising:
   a non-ionic hydrophilic branched polysaccharide at a density, wherein, if the composition is contacted with whole blood and centrifuged, said density is sufficient to permit fluid movement of whole blood through the non-ionic hydrophilic branched polysaccharide without separation of erythrocytes,
   the non-ionic hydrophilic branched polysaccharide having a molecular weight greater than 20 kDa; and
   a TLR2 ligand,
   wherein the composition is contained within the container, and wherein the container is sterile.
2. The bone marrow container of option 1, wherein the non-ionic hydrophilic branched polysaccharide has a molecular weight of at least 70 kDa.
3. The bone marrow container of any one of options 1-2, wherein the non-ionic hydrophilic branched polysaccharide comprises poly(sucrose-co-epichlorhydrin).
4. The bone marrow container of any one of options 1-3, wherein the non-ionic hydrophilic branched polysaccharide has a density less than 1 gram per liter.
5. The bone marrow container of any one of options 1-4, wherein the TLR2 ligand is selected from the group consisting of hyaluronon, hyaluronic acid, monosodium urate crystals, biglycan, endoplasmin, HMGB1, HSP60, HSP70, human cardiac myosin, zymosan, lipoteichoic acids, lipoproteins from plasma, lipopolysaccharide (LPS), and peptidoglycans including Pam2CSK4 and Pam3CSK4.
6. The bone marrow container of option 1, wherein the non-ionic hydrophilic branched polysaccharide comprises poly(sucrose-co-epichlorhydrin) at a density of less than 1 gram per liter, and wherein the TLR2 ligand comprises hyaluronic acid.
7. The bone marrow container of any one of options 1-6, wherein the container is selected from the group consisting of a bag, a vacutainer, and a syringe.
8. The bone marrow container of any one of options 1-7, further comprising an integral delivery device.
9. The bone marrow container of any one of options 1-8, further comprising dextran.
10. The bone marrow container of option 9, wherein the dextran is at a concentration of at least about 4%.
11. The bone marrow container of any one of options 9-10, further comprising a volume configured to receive bone marrow, wherein, when bone marrow is present in the volume, the concentration of the dextran in the bone marrow and the composition is at least about 1%.
12. The bone marrow container of any one of options 9-11, wherein the container is configured to be received by a separation system.
13. A separation system comprising:
    A chassis comprising a cavity configured to receive the bone marrow container of any one of options 1-12, the chassis comprising a track; and
    a shaft disposed on the track, wherein the shaft is configured to move along the track, thereby compressing the bone marrow container when the bone marrow container is disposed in the chassis.
14. The separation system of option 13, wherein the shaft is configured to compress the bone marrow container against an inner surface of the chassis.
15. The separation system of any one of options 13-14, wherein the shaft is selected from the group consisting of a roller and a slider.
16. The separation system of any one of options 13-14, wherein the shaft is configured to snap into position against a bone marrow container disposed in the chassis, thereby defining at least two portions of the bone marrow container.
17. A kit comprising the bone marrow container of any one of options 1-12, and a bone marrow aspiration needle such as a luer lock.
18. The kit of option 17, further comprising a filter, the filter having a pore size smaller than a diameter of a myeloid cell.
19. The kit of option 18, wherein the pore size is less than or equal to 200 microns.
20. The kit of any one of options 17-19, further comprising an activation/sedimentation solution.
21. The kit of any one of options 17-20, further comprising the separation system of any one of options 13-16.
22. A method of activating immune cells of a subject, the method comprising:
    obtaining bone marrow of the subject, the bone marrow comprising immune cells;
    incubating the bone marrow with a non-ionic hydrophilic branched polysaccharide and a TLR2 ligand,
        wherein the non-ionic hydrophilic branched polysaccharide is at a density, wherein, if the bone marrow is contacted with whole blood and centrifuged, said density is sufficient to permit fluid movement of whole blood through the non-ionic hydrophilic branched polysaccharide without separation of erythrocytes,
        wherein the non-ionic hydrophilic branched polysaccharide has a molecular weight greater than 20 kDa, and
        wherein the incubating is performed until the immune cells are activated; and
    administering the activated immune cells to the subject.
23. The method of option 22, further comprising identifying a subject as being in need of immune cell activation.
24. The method of option 23, wherein the subject has cancer.
25. The method of option 24, wherein the incubating further comprises incubating the bone marrow with a cancer cell antigen.
26. The method of any one of options 22-25, wherein the non-ionic hydrophilic branched polysaccharide has a molecular weight of at least 70 kDa.
25. The method of any one of options 22-26, wherein the non-ionic hydrophilic branched polysaccharide comprises poly(sucrose-co-epichlorhydrin).
26. The method of any one of options 22-27, wherein non-ionic hydrophilic branched polysaccharide has a density less than 1 gram per liter.
27. The method of any one of options 22-28, wherein the TLR2 ligand is selected from the group consisting of hyaluronon, hyaluronic acid, monosodium urate crystals, biglycan, endoplasmin, HMGB1, HSP60, HSP70, human cardiac myosin, zymosan, lipoteichoic acids, lipoproteins from plasma, LPS, and peptidoglycans including Pam2CSK4 and Pam3CSK4.
28. The method of options 22, wherein the non-ionic hydrophilic branched polysaccharide comprises poly (sucrose-co-epichlorhydrin) at a density of less than 1 gram per liter, and wherein the TLR2 ligand comprises hyaluronic acid.

29. The method of any one of options 23-27, wherein the non-ionic hydrophilic branched polysaccharide comprises poly(sucrose-co-epichlorhydrin) at a density of less than 1 gram per liter, and wherein the TLR2 ligand comprises hyaluronic acid.

30. The method of any one of options 22-29, wherein the incubating is performed in the bone marrow container of any one of options 1-16.

31. The method of option 30, further comprising:
disposing the bone marrow container in the separation system of any one of options 17-21;
snapping the shaft into position against the bone marrow container, thereby defining two portions of the bone marrow container;
after said incubating, moving the shaft along the track, thereby compressing the contents of the bone marrow container, and extruding immune cells from the bone marrow.

32. The method of any one of options 22-31, further comprising incubating the bone marrow with an activation/sedimentation solution, thereby sedimenting red blood cells from the bone marrow.

33. The method of any one of options 22-32, wherein the activated immune cells comprise myeloid cells.

34. The method of option 33 wherein the activated immune cells comprise CD11b$^+$ CD54$^+$ granuloyctes and/or CD66b+ neutrophils.

35. The method of any one of options 22-34, further comprising separating the activated immune cells from the non-ionic hydrophilic branched polysaccharide and the TLR2 ligand prior to administering the activated immune cells to the subject.

36. The method of any one of options 22-35, wherein the activated immune cells are administered to a musculo-skeletal tissue of the subject.

37. The method of any one of options 22-36, wherein the method does not comprise leukaphoresis.

In general, conventional methods of separation exploited different physical characteristics of RBCs to enrich in the mononuclear cell fraction which contains the HSCs and MSCs. Density-mediated separation conventionally used Percoll and FICOLL-HIPAQUE polysaccharides, at densities greater than 1.0 and applied centrifugal force to accomplish the physical separation. This could allow a mononuclear cell fraction to be used which contains the regenerative cells in a smaller and more useful volume, as the marrow was de-bulked by removal of RBCs, and granulocytes.

Without being limited by theory, it is contemplated that the non-ionic hydrophilic branched polysaccharides of some embodiments can activate regenerative cells in bone marrow using a mechanism similar to or analogous to bacterial cell wall polysaccharides which can activate the innate arm of the human immune system. Without being limited by theory, it is contemplated that a TLR2 ligand of some embodiments can activate myeloid cells, and that activation of myeloid cells can enhance their therapeutic effectiveness. Thus, it is contemplated that activating immune cells using non-ionic hydrophilic branched polysaccharides and a TLR2 ligand in accordance with compositions, bone marrow containers, kits, and methods described herein can enhance the efficacy of treating patients with autologous bone marrow cells.

EXAMPLE 1

Flow cytometric analysis of myeloid dendritic cell activation after exposure of bone marrow aspirate to FICOLL polysaccharide and the following TLR2 ligands: lipoproteins from plasma, synthetic PAM-3CSK4, and lipopolysaccharide (LPS). Samples of peripheral blood (PB) and bone marrow (BM) were obtained from a single donor, and all samples were treated with hypertonic salt solution (FACS Lysing solution, Becton Dickinson) to remove erythrocytes, prior to staining using a no wash method. The appropriate, fluorochrome-conjugated monoclonal antibodies were then incubated in PBS with 2% bovine serum albumin for 30 minutes on ice according to manufacturer's instructions, and data was collected immediately on greater than 50,000 events. Gates were set using isotype-matched controls. It is noted that the PB control provides a positive control for relatively rare mature dendritic cells. The dendritic cells were compared between negative control bone marrow cells and matched bone marrow after exposure to TLR-ligand and Ficol diluted 1/100 (v/v).

FIG. 1A and FIG. 1D (peripheral blood sample positive control, PB), FIG. 1B and FIG. 1E (whole bone marrow negative control prior to exposure to FICOLL polysaccharide and TLR2 agonists), and FIG. 1C and FIG. 1F (bone marrow aspirate mononuclear cells (MNC) after exposure to Ficol and TLR2 agonists, MNC). Lineage negative, CD14 negative, myeloid size-gated classical dendritic cells (FIG. 1A, FIG. 1B, and FIG. 1C; white arrows 1, 2, and 3 denote dendritic cells in regions 1, 2, and 3) and gated dendritic cells were analyzed for activation by measuring the percentage of activated cells for HLA-DR (a marker of maturation) expression by percentage positive and relative fluorescence intensity (FIG. 1D, FIG. 1E, and FIG. 1F).

FIG. 1D (PB positive control) FIG. 1E (BM negative control) white arrow number 5 shows control levels of myeloid cell activation for the whole bone marrow negative control, while FIG. IF white arrow 6 shows up-regulation of HLA-DR in both the percentage of cells positive (1.9 vs 15.9%) and relative mean fluorescence intensity after overnight exposure to TLR-2 ligands and Ficoll at less than 1.0 gm/L. FIG. 1D white arrow 4 shows control levels of myeloid cell activation for the PB control.

Thus, it can concluded that in accordance with some embodiments herein, immune cells were activated by incubation of bone marrow with FICOLL polysaccharide and TLR2 ligand in accordance with some embodiments herein. Moreover, dendritic cell maturation from myeloid progenitors is increased by the activation.

EXAMPLE 2

Figure 2G:
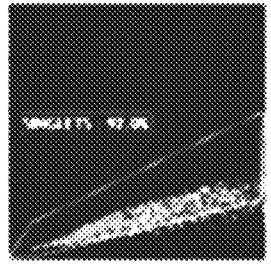
Figure 2H:
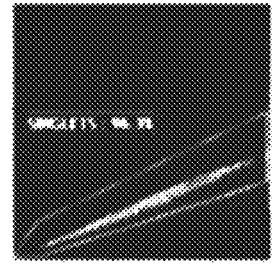
Figure 2I:
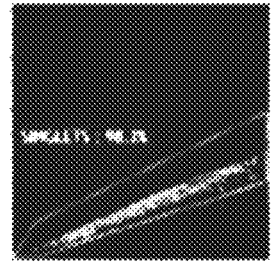

Further analysis of activated bone marrow cells activated with FICOLL polysaccharide and TLR2 ligand of Example 1) was performed. The gating scheme is shown in FIGS. 2A-I. Cells were gated according to size (FIGS. 2A-C), viability (sytox blue staining)(FIGS. 2D-F), and for singlets (FIGS. 2G-I).

Phenotypic characterization of the cells showed that the population of activated immune cells comprised immature (CD33-low, CD11b-low) myeloid cells. CD66b was expressed by neutrophils, indicating a novel DC population. Thus, it can be concluded that immature myeloid cells such as neutrophils were activated in accordance with some embodiments herein.

EXAMPLE 3

A patient is aspirated and approximately 25 mls of whole bone marrow is processed by either Terumo BCT SmartPrep bone marrow aspirate concentration (BMAC) or using a Biomet Marrow stim system, both according to manufacturer's instructions (though it is contemplated that in accordance with some embodiments herein, any device currently marketed for bone marrow processing and de-bulking can be used). The resulting marrow concentrate is then injected into a sterile bone marrow container containing a 100× concentration of a sufficient amount of Ficoll-Hypaque and hyaluronic acid to increase CD11b expression by flow cytometry or gene expression analysis, then allowed to incubate at ambient temperature at the point-of-care, for at least 10 minutes and no greater than 8 hours. The cells are then filtered such that cells are retained, and the activating moieties are significantly reduced in concentration, and the activated cells are then delivered to a patient. Surgical procedures that implant medical devices, including allogeneic biologic tissues, synthetic bone fillers, hardware associated with spinal and other surgeries such as stainless steel, titanium or PEEK devices used to support musculoskeletal tissue regeneration are improved and outcomes are enhanced compared to bone marrow concentrates which are not processed using the disclosed compositions and methods of embodiments herein.

In some embodiments, the method, use, or composition comprises various steps or features that are present as single steps or features (as opposed to multiple steps or features). For example, in some embodiments, the method includes a single incubation of bone marrow with a non-ionic hydrophilic branched polysaccharide and a TLR2 ligand. The non-ionic hydrophilic branched polysaccharide and a TLR2 ligand may be present in an amount effective for activating immune cells such as myeloid cells. A method, bone marrow container, or kit may comprise a single quantity of hydrophilic branched polysaccharide and a TLR2 ligand effective for activating immune cells as described herein. Multiple features or components are provided in alternate embodiments.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. For each method of described herein, relevant compositions for use in the method are expressly contemplated, uses of compositions in the method, and, as applicable, methods of making a medicament for use in the method are also expressly contemplated. For example, for methods of activating immune cells described herein, compositions comprising a hydrophilic branched polysaccharide and a TLR2 ligand (and bone marrow containers) for use in the corresponding method are also contemplated. Additionally, in vitro methods that do involve treatment of a patient are contemplated, for example, a method comprising receiving bone marrow aspirate, and incubating the bone marrow aspirate with hydrophilic branched polysaccharide and a TLR2 ligand in vitro, thus activating immune cells in vitro. One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., " a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. For example, "about 5", shall include the number 5. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A bone marrow container comprising: a composition comprising:
    a non-ionic hydrophilic branched polysaccharide at a concentration, wherein, if the composition is contacted with whole blood and centrifuged, said concentration is sufficient to permit fluid movement of whole blood through the non-ionic hydrophilic branched polysaccharide without separation of erythrocytes, wherein the non-ionic hydrophilic branched polysaccharide comprises poly(sucrose-co-epichlorhydrin),
    the non-ionic hydrophilic branched polysaccharide having a molecular weight greater than 20 kDa; and
    a TLR2 ligand, wherein the composition is contained within the container, and wherein the container is sterile.

2. The bone marrow container of claim 1, wherein the non-ionic hydrophilic branched polysaccharide has a molecular weight of at least 70 kDa.

3. The bone marrow container of any one of claim 1, wherein the non-ionic hydrophilic branched polysaccharide has a density less than 1 gram per liter.

4. The bone marrow container of claim 1, wherein the TLR2 ligand is selected from the group consisting of hyaluronon, hyaluronic acid, monosodium urate crystals, biglycan, endoplasmin, HMGB1, HSP60, HSP70, human cardiac myosin, zymosan, lipoteichoic acids, peptidoglycans, and Pam2CSK4, and Pam3CSK4.

5. The bone marrow container of claim 1, wherein the non-ionic hydrophilic branched polysaccharide comprises poly(sucrose-co-epichlorhydrin) at a concentration of less than 1 gram per liter, and wherein the TLR2 ligand comprises hyaluronic acid.

6. The bone marrow container of claim 1, further comprising an integral delivery device.

7. The bone marrow container of claim 1, further comprising dextran.

8. A kit comprising the bone marrow container of claim 1, and a bone marrow aspiration needle.

9. The bone marrow container of claim 3, wherein the concentration of the non-ionic hydrophilic branched polysaccharide is less than 0.99 g/l, 0.9 g/l, 0.8 g/l, 0.7 g/l, 0.6 g/7, 0.5 g/l, 0.4 g/l, 0.3 g/l, 0.2 g/l, 0.1 g/l, 0.05 g/l, $10^{-2}$ g/l, $2\times10^{-3}$ g/l, $10^{-3}$ g/l, $10^{-5}$ g/l, $2\times10^{-6}$ g/l, $10^{-6}$ g/l, $10^{-7}$ g/l, $10^{-8}$ g/l, $2\times10^{-9}$ g/l, or $10^{-9}$ g/l.

10. The bone marrow container of claim 3, wherein the concentration of the non-ionic hydrophilic branched polysaccharide is $10^{-9}$ to $10^{-6}$ g/L, $10^{-9}$ to $10^{-3}$ g/L, $10^{-9}$ to $10^{-2}$ g/L, $10^{-9}$ to 0.1 g/L, $10^{-9}$ to 0.5 g/L, $10^{-9}$ to 0.9 g/L, $10^{-9}$ to 0.09 g/L, $10^{-6}$ to $10^{-3}$ g/L, $10^{-6}$ to $10^{-2}$ g/L, $10^{-6}$ to 0.1 g/L, $10^{-6}$ to 0.5 g/L, $10^{-6}$ to 0.9 g/L, $10^{-6}$ to 0.09 g/L, $2\times10^{-6}$ to $10^{-3}$ g/L, $2\times10^{-6}$ to $10^{-2}$ g/L, $2\times10^{-6}$ to 0.1 g/L, $2\times10^{-6}$ to 0.5 g/L, $2\times10^{-6}$ to 0.9 g/L, $2\times10^{-6}$ to 0.09 g/L, $10^{-3}$ to $10^{-2}$ g/L, $10^{-3}$ to 0.1 g/L, $10^{-3}$ to 0.5 g/L, $10^{-3}$ to 0.9 g/L, $10^{-3}$ to 0.09 g/L, $2\times10^{-3}$ to $10^{-2}$ g/L, $2\times10^{3}$ to 0.1 g/L, $2\times10^{-3}$ to 0.5 g/L, $2\times10^{3}$ to 0.9 g/L, $2\times10^{-3}$ to 0.09 g/L, 0.01 to 0.99 g/L, 0.01 to 0.9 g/L, 0.01 to 05. g/L, 0.01 to 0.2 g/L, 0.01 to 0.1 g/L, 0.1 to 0.99 g/L, 0.1 to 0.9 g/L, 0.1 to 0.5 g/L, 0.1 to 0.2 g/L, 0.5 to 0.99 g/L, 0.5 to 0.9 g/L, or 0.5 to 0.7 g/L.

* * * * *